(12) United States Patent
Itoh et al.

(10) Patent No.: US 7,160,545 B2
(45) Date of Patent: Jan. 9, 2007

(54) HLA-A24 BINDING PEPTIDES OF ENHANCER OF ZESTE HOMOLOG 2

(75) Inventors: Kyogo Itoh, Miyaki-gun (JP); Mamoru Harada, Fukuoka (JP)

(73) Assignee: Green Peptide Co., Ltd., Fukuoka (JP)

( * ) Notice: Subject to any disclaimer, the term of this patent is extended or adjusted under 35 U.S.C. 154(b) by 0 days.

(21) Appl. No.: 11/208,541

(22) Filed: Aug. 23, 2005

(65) Prior Publication Data

US 2005/0287160 A1 Dec. 29, 2005

(51) Int. Cl.
*A61K 39/00* (2006.01)
*A61K 39/38* (2006.01)

(52) U.S. Cl. .................................. 424/184.1
(58) Field of Classification Search .............. 424/184.1
See application file for complete search history.

(56) References Cited

U.S. PATENT DOCUMENTS 5,925,388 A * 7/1999 Moineau et al. ............... 426/43
6,689,583 B1 * 2/2004 Jenuwein et al. .......... 435/69.1

OTHER PUBLICATIONS

Bowie et al (Science, 1990, 257:1306-1310).*
Burgess et al (J of Cell Biol. 111:2129-2138, 1990).*
Lazar et al (Molecular and Cellular Biology, 1988, 8:1247-1252).*
R. T. Greenlee et al., "Cancer Statistics, 2000", CA Cancer J. Clin., vol. 50, No. 1, pp. 7-33, Jan./Feb. 2000.
M. Harada et al., "Target molecules in specific immunotherapy against prostate cancer", Intl. J. Clinical Oncology, vol. 8, pp. 193-199, 2003.
J. Gulley et al., "Phase I Study of a Vaccine using Recombinant Vaccinia Virus Expressing PSA (rV-PSA) in Patients with Metastatic Androgen-Independent Prostate Cancer", The Prostate, vol. 53, pp. 109-117, 2002.
G. Murphy et al., "Phase I Clinical Trial: T-Cell Therapy for Prostate Cancer using Autologous Dendritic Cells Pulsed with HLA-A0201-Specific Peptides from Prostate-Specific Membrane Antigen", The Prostate, vol. 29, pp. 371-380, 1996.
B. A. Tjoa et al., "Evaluation of Phase I/II Clinical Trials in Prostate Cancer with Dendritic Cells and PSMA Peptides", The Prostate, vol. 36, pp. 39-44, 1998.
G. P. Murphy et al., "Infusion of Dendritic Cells Pulsed with HLA-A2-Specific Prostate-Specific Membrane Antigen Peptides: A Phase II Prostate Cancer Vaccine Trial Involving Patients with Hormone-Refractory Metastatic Disease", The Prostate, vol. 38, pp. 73-78, 1999.

E. J. Small et al., "Immunotherapy of Hormone-Refractory Prostate Cancer with Antigen-Loaded Dendritic Cells" Journal of Clinical Oncology, vol. 18, No. 23, pp. 3894-3903, Dec. 1, 2000.
G. Laible et al., "Mammalian homologues of the Polycomb-group gene Enhancer of zeste mediate gene silencing in *Drosophila heterochromatin* and at *S. cerevisiae* telomeres", The EMBO Journal, vol. 16, No. 11, pp. 3219-3232, 1997.
C. G. Kleer et al., "EZH2 is a marker of aggressive breast cancer and promotes neoplastic transformation of breast epithelial cells", PNAS, vol. 100, No. 20, pp. 11606-11611, Sep. 30, 2003.
J. J. L. Jacobs et al., "The oncogene and polycomb-group gene *bmi*-1 regulates cell proliferation and senescence through the *ink*4a locus", Letters to Nature, vol. 397, pp. 164-168, Jan. 1999.
J. J. L. Jacobs et al., "Bmi-1 collaborates with c-Myc in tumorigenesis by inhibiting c-Myc-induced apoptosis via INK4a/ARF", Genes & Development, vol. 13, pp. 2678-2690, 1999.
S. Varambally et al., "The polycomb group protein EZH2 is involved in progression of prostate cancer", Letters to Nature, vol. 419, pp. 624-629, Oct. 10, 2002.
M. Noguchi et al., "Induction of Cellular and Humoral Immune Responses to Tumor Cells and Peptides in HLA-A24 Positive Hormone-Refractory Prostate Cancer Patients by Peptide Vaccination", The Prostate, vol. 57, pp. 80-92, 2003.
S. Tanaka et al., "Peptide Vaccination for Patients with Melanoma and other Types of Cancer based on Pre-existing Peptide-Specific Cytotoxic T-Lymphocyte Precursors in the Periphery", Journal of Immunotherapy, vol. 26, No. 4, pp. 357-366, Jul./Aug. 2003.
T. Mine et al., "Immunological evaluation of CTL precursor-oriented vaccines for advanced lung cancer patients", Cancer Science, vol. 94, No. 6, pp. 548-556, Jun. 2003.
Y. Sato et al., "Immunological evaluation of peptide vaccination for patients with gastric cancer based on pre-existing cellular response to peptide", Cancer Science, vol. 94, No. 9, pp. 802-808, Sep. 2003.
N. Tsuda et al., "Vaccination with Predesignated or Evidence-Based Peptides for Patients with Recurrent Gynecologic Cancers", J. Immunother, vol. 27, No. 1, pp. 60-72, Jan./Feb. 2004.

(Continued)

*Primary Examiner*—Susan Ungar
*Assistant Examiner*—Catherine Joyce
(74) *Attorney, Agent, or Firm*—Wenderoth, Lind & Ponack, L.L.P.

(57) ABSTRACT

A cancer antigen peptide comprising an amino acid sequence shown in SEQ ID NO: 1 or 2, or a derivative thereof having the functionally equivalent property is provided. The provided cancer antigen peptide is a partial peptide derived from enhancer of zeste homolog 2, which is capable of binding to HLA-A24 antigen and is recognized by cytotoxic T lymphocytes. The cancer antigen peptide of the invention is useful for treatment and prevention of prostate cancer.

1 Claim, 6 Drawing Sheets

OTHER PUBLICATIONS

T. Nakatsura et al., "Cellular and humoral immune responses to a human pancreatic cancer antigen, coactosin-like protein, originally defined by the SEREX method", Eur. J. Immunol., vol. 32, pp. 826-836, 2002.

K. C. Parker et al., "Scheme for Ranking Potential HLA-A2 Binding Peptides Based on Independent Binding of Individual Peptide Side-Chains", J. Immunol., vol. 152, pp. 163-175, 1994.

S. Ohkouchi et al., "Non-mutated tumor-rejection antigen peptides elicit type-I allergy in the majority of healthy individuals", Tissue Antigens, vol. 59, pp. 259-272, 2002.

N. Hida et al., "A simple culture protocol to detect peptide-specific cytotoxic T lymphocyte precursors in the circulation", Cancer Immunol. Immunother, vol. 51, pp. 219-228, 2002.

N. Kawamoto et al., "IgG reactive to CTL-directed epitopes of self-antigens is either lacking or unbalanced in atopic dermatitis patients", Tissue Antigens, vol. 61, pp. 352-361, 2003.

M. Harada et al., "Prostate-Specific Antigen-Derived Epitopes Capable of Inducing Cellular and Humoral Responses in HLA-A24+ Prostate Cancer Patients", The Prostate, vol. 57, pp. 152-159, 2003.

K. Kobayashi et al., "Identification of a prostate-specific membrane antigen-derived peptide capable of eliciting both cellular and humoral immune responses in HLA-A24+ prostate cancer patients", Cancer Science, vol. 94, No. 7, pp. 622-627, Jul. 2003.

S. Matsueda et al., "Identification of new prostate stem cell antigen-derived peptides immunogenic in HLA-A2+ patients with hormone-refractory prostate cancer", Cancer Immunol. Immunother, vol. 53, pp. 479-489, 2004.

Y. Inoue et al., "Induction of Tumor Specific Cytotoxic T Lymphocytes in Prostate Cancer using Prostatic Acid Phosphatase Derived HLA-A2402 Binding Peptide", The Journal of Urology, vol. 166, pp. 1508-1513, Oct. 2001.

T. Imanishi et al., "Allele and haplotype frequencies for HLA and complement loci in various ethnic groups", HLA 1991, vol. 1, Oxford: Oxford Scientific Publications, 1992, pp. 1065-1220.

M. Harada et al., "In Vivo Evidence that Peptide Vaccination can Induce HLA-DR-Restricted CD4+ T Cells Reactive to a Class I Tumor Peptide", The Journal of Immunology, vol. 172, pp. 2659-2667, 2004.

* cited by examiner

EZH2

GAPDH

HLA-A24 BINDING PEPTIDES OF ENHANCER OF ZESTE HOMOLOG 2

TECHNICAL FIELD

The invention relates to a cancer antigen peptide derived from enhancer of zeste homolog 2 (EZH2) immunogenic in human histocompatibility leukocyte antigen (HLA)-A24+ prostate cancer patients. The cancer antigen peptide of the present invention is useful for treating prostate cancer.

BACKGROUND OF THE INVENTION

Prostate cancer is one of the most common cancers among elder men (1). Prostate cancer frequently metastasizes to bone, and androgen withdrawal therapy has been applied for such patients. However, there is no efficient therapy against hormone-refractory and metastatic prostate cancer. Therefore, there is an urgent need for the development of new therapeutic modalities, and specific immunotherapy is one candidate. Indeed, prostate tissue-specific antigens expressed in the normal prostate can be target molecules for specific immunotherapy (2). Specific immunotherapy targeting prostate tissue-specific antigens has been carried out, and, in recent years, the inventors have identified several epitope peptides derived from prostate-related antigens that are able to generate prostate cancer-reactive cytotoxic T lymphocytes (CTLs) from prostate cancer patients (23–26). However, one major obstacle encountered when treating prostate cancer patients is the treatment of bone metastases, as prostate cancer frequently metastasizes to the bone tissue (1). Thus, the clinical responses remain unsatisfactory (3–7).

Enhancer of zeste homolog 2 (EZH2) is a polycomb group protein homologous to the Drosophila enhancer of zeste, and is involved in gene silencing (8). Dysregulation of this gene-silencing machinery can lead to cancer (9–11). In addition, it has been reported that EZH2 is overexpressed in metastatic prostate cancer and functions as a transcriptional repressor, and that inhibition of EZH2 blocks growth of prostate cancer cells (12).

In our clinical trials against several types of cancer, several class I-binding cancer antigen-derived peptides that had originally been identified by their ability to induce cancer-reactive CTLs were also recognized by immunoglobulin G (IgG) (13, 14). Additional clinical trials revealed that the induction of IgG reactive to administered peptides was positively correlated with the overall survival of cancer patients (15–17). These lines of evidence suggest that peptides that can be recognized by both the humoral and cellular immune systems might be more useful for immunotherapy than peptides that can be recognized by only one of the two systems. In addition, the assay for peptide-specific IgG is much simpler and easier than the in vitro sensitization experiment to induce peptide-specific CTLs (18).

SUMMARY OF THE INVENTION

An object of the present invention is to provide a cancer antigen peptide that is useful in specific immunotherapy for prostate cancer, especially for metastatic prostate cancer.

A further object of the present invention is to provide a method for treating prostate cancer with the cancer antigen peptide of the present invention.

As described above, it would be believed that peptides that can be recognized by both the humoral and cellular immune systems might be more useful for immunotherapy than peptides that can be recognized by only one of the two systems. Along with this line, we first screened EZH2-derived peptide candidates by their ability to be recognized by the humoral immune system, and then determined their potential to induce peptide-specific and prostate cancer-reactive CTLs. As a consequence, we identified two EZH2-derived peptides that are efficiently recognized by both the humoral and cellular immune systems in HLA-A24+ prostate cancer patients.

Eleven EZH2-derived peptides were prepared based on the HLA-A24 binding motif. These peptide candidates were screened first by their ability to be recognized by IgG, and then by their ability to induce peptide-specific CTLs. IgGs reactive to three EZH2 peptides (EZH2 243–252, EZH2 291–299, and EZH2 735–743) were detected in the plasma of almost half of prostate cancer patients. Among them, the EZH2 291–299 and EZH2 735–743 peptides efficiently induced HLA-A24-restricted and prostate cancer-reactive CTLs from prostate cancer patients. The cytotoxicity was mainly dependent on EZH2 peptide-specific and CD8+ T cells.

The frequencies of the HLA-A24 allele are relatively high throughout the world (27). The EZH2 291–299 (SEQ ID No. 1) and EZH2 735–743 (SEQ ID No. 2) peptides could be promising candidates for peptide-based immunotherapy for HLA-A24+ prostate cancer patients with metastases.

Thus, the present invention provides a cancer antigen peptide derived from human EZH2, which is capable of binding to HLA-A24 antigen and is recognized by CTLs. Especially, the cancer antigen peptide comprising an amino acid sequence shown in SEQ ID NO: 1 or 2, or a derivative thereof having the functionally equivalent property is provided.

Also provided is a method for treating or preventing prostate cancer, which comprises administering at least one of the cancer antigen peptides and derivatives of the present invention to a patient in need thereof. According to the present invention, the prostate cancer may be that associated with bone metastases. The invention further provides a method for treating or preventing pathological bone metastases accompanied by the prostate cancer.

The present invention further provides a CTL that specifically recognizes complex of HLA-A24 antigen and the cancer antigen peptide or derivative of the present invention.

The present invention still further provides a method for treating prostate cancer, which comprises administering the above-defined CTL to a patient in need thereof. The prostate cancer may be associated with bone metastases. In addition, the present invention also provides a method for treating or preventing pathological bone metastases accompanied by the prostate cancer.

DETAILED DESCRIPTION OF THE PREFERRED EMBODIMENTS

As used herein, the term "EZH2" is human polycomb group protein homologous to the Drosophila enhancer of zeste. EZH2 is a 746-amino-acid polypeptide that shows 60.5% identity to the Drosophila enhancer of zeste and contains a trithorax-like domain and a DNA-binding motif. The amino acid sequence is described in Chen, H., Rossier, C., Antonarakis, S. E., Cloning of a human homolog of the Drosophila enhancer of zeste gene (EZH2) that maps to chromosome 21q22.2. (1996), Genomics 38:30–37 (this reference is incorporated herein by reference). According to the invention, the cancer antigen peptide is a part of EZH2 that is capable of binding to HLA-A24 antigen and is recognized by CTLs. The cancer antigen peptide is recognized by CTLs in a form of complex with HLA antigen.

Synthesis of peptides may be conducted according to a method usually used in peptide chemistry. Examples of the known methods are those described in the literatures including "Peptide Synthesis", Interscience, New York, 1966; "The Proteins", vol. 2, Academic Press Inc., New York, 1976; "Pepuchido-Gosei", Maruzen Co. Ltd., 1975 (these references are incorporated herein by reference).

As used herein, the term "derivative of a cancer antigen peptide" means an altered peptide of which amino acid sequence contains a substitution, deletion and/or addition of one to several, preferably one or two amino acid residues in the amino acid sequence of the cancer antigen peptide of the present invention (SEQ ID Nos. 1 or 2). "The functionally equivalent property" means the property as a cancer antigen peptide, i.e., the derivative is capable of binding to HLA-A24 antigen and is recognized by CTLs. Considering the binding to HLA antigen, the derivative of the present invention is preferably 8 to 14, more preferably 8 to 11 amino acids long.

The sequence rules (motifs) of a peptide for the binding to an HLA-A24 antigen have been known in the art (J. Immunol., 152:163, 1994; Immunogenetics, 41:178, 1995, these references are incorporated herein by reference). It is preferable that, when the derivative of the present invention comprises one or two substitutions, the substitutions are those accepted in view of the motifs.

The cancer antigen peptide or derivative of the present invention can be used for treating or preventing prostate cancer, especially prostate cancer associated with bone metastases. In the present invention, "treatment of prostate cancer" includes treatment or prevention of pathological bone metastases accompanied by the prostate cancer.

According to the method of the present invention, at least one of the cancer antigen peptides or derivatives of the present invention is administered to the patient, if necessary, in combination with other anti-cancer agents such as immunomodulators or chemotherapeutics. When administered, the cancer antigen peptide or the derivative will be presented on the antigen-presenting cells at a high density in a form of complex with HLA-A24 antigen. CTLs specific for the presented HLA antigen complex will proliferate upon the presentation of the complex and destroy cancer cells presenting the corresponding HLA antigen complex. As a result, the cancer of the patient may be treated, or proliferation or metastasis of the cancer cells may be prevented.

In this embodiment, the cancer antigen peptide or derivative of the present invention may be administered along with an adjuvant in order to effectively establish the cellular and/or humoral immunity. Administration may be conducted intradermally, hypodermically, or by intravenous injection. The amount of the cancer antigen peptide or derivative of the present invention to be administered may vary depending on, for example, the condition of the disease to be treated, the age and the body weight of the particular patient. In general, 0.1 mg to 10.0 mg, preferably 0.5 mg to 5.0 mg, more preferably 1.0 mg to 3.0 mg of the peptide or derivative of the invention may be administered every several days, week, or months.

Additionally, the present invention provides CTLs that specifically recognize complex of HLA-A24 antigen and the cancer antigen peptide or derivative of the present invention, and also provides a method for treating prostate cancer which comprises administering the CTLs to the patient in need thereof. The method for inducing CTLs which recognize specifically complex of HLA-24 antigen and the cancer antigen or derivative of the present invention is well known to the art. The CTL may be dispersed in physiological saline or phosphate buffered saline (PBS) and administered, for example, intravenously, subcutaneously, or intradermally.

EXAMPLES

The present invention is further illustrated by the following examples, but is not limited by these examples in any respect. In the following examples, only the position number of the starting amino acid of EZH2 peptides is shown to show each of the peptides. The statistical significance of the data was determined using a two-tailed Student's t-test. A P value of less than 0.05 was considered to be statistically significant.

Example 1

Assay for IgG Reactive to EZH2-derived Peptides 1.1 Patients

All prostate cancer patients in this study provided their informed consent before enrollment. None of these participants was infected with human immunodeficiency virus (HIV). Twenty milliliters of peripheral blood was obtained, and the peripheral blood mononuclear cells (PBMCs) were prepared by Ficoll-Conray density gradient centrifugation. The expression of HLA-A24 molecules on the PBMCs of cancer patients and healthy donors was determined by flow cytometry.

1.2 Peptides

Eleven EZH2-derived peptides (listed in Table 1) were prepared based on the HLA-A24 binding motif (19). All peptides were of >90% purity and were purchased from Biologica Co., Nagoya, Japan. Influenza (Flu) virus-derived (RFYIQMCYEL SEQ ID NO: 12), EBV-derived (TYGPVFMCL SEQ ID NO: 13), and HIV-derived peptides (RYLRDQQLLGI SEQ ID NO: 14) with the HLA-A24 binding motif were used as controls. All peptides were dissolved with DMSO at a concentration of 10 mg/ml.

TABLE 1

A list of EZH2-derived peptides

| Position | Amino acid sequence | Score |
|---|---|---|
| 291–299 | KYDCFLHPF (SEQ ID NO: 1) | 200.0 |
| 735–743 | KYVGIEREM (SEQ ID NO: 2) | 115.5 |
| 657–665 | VYDKYMCSF (SEQ ID NO: 3) | 100.0 |
| 446–454 | TYYDNFCAI (SEQ ID NO: 4) | 72.0 |
| 170–178 | IFVELVNAL (SEQ ID NO: 5) | 51.8 |
| 90–98 | DFPTQVIPL (SEQ ID NO: 6) | 30.0 |
| 660–669 | KYMCSFLFNL (SEQ ID NO: 7) | 600.0 |
| 243–252 | KYKELTEQQL (SEQ ID NO: 8) | 576.0 |

TABLE 1-continued

A list of EZH2-derived peptides

| Position | Amino acid sequence | Score |
|---|---|---|
| 725–734 | DYRYSQADAL (SEQ ID NO: 9) | 200.0 |
| 657–666 | VYDKYMCSFL (SEQ ID NO: 10) | 200.0 |
| 119–128 | NFMVEDETVL (SEQ ID NO: 11) | 30.0 |

Scores represent the estimated half-time dissociation of the EZH2 peptide binding to HLA-A24 molecules.

1.3 Detection of Peptide Specific IgG

Peptide-specific IgG levels in the plasma were measured by ELISA using a previously reported method (20). In brief, peptide (20 μg/well)-immobilized plates were blocked with Block Ace (Yukijirushi, Tokyo, Japan) and washed with 0.05% Tween20-PBS, after which 100 μl/well of plasma sample diluted with 0.05% Tween20-Block Ace was added to the plates. After a 2-hr incubation at 37° C., the plates were washed and further incubated for 2 hr with a 1:1000-diluted rabbit anti-human IgG (γ-chain-specific) (DAKO, Glostrup, Denmark). The plates were washed, and then 100 μl of 1:100-diluted goat anti-rabbit IgG-conjugated horseradish peroxidase (EnVision; DAKO) was added to each well, and the plates were incubated at room temperature for 40 min. After the plates were washed once, 100 μl/well of tetramethyl benzidine substrate solution (KPL, Guildford, UK) was added, and the reaction was stopped by the addition of 1 M phosphoric acid. The values are shown as optical density (OD) units/ml. To confirm the specificity of IgG to the indicated EZH2 peptide, sample plasma was cultured with plates coated with either the corresponding EZH2 peptide or an irrelevant EZH2 peptide. Thereafter, the levels of EZH2 peptide-specific IgG in the resulting supernatant were determined by ELISA.

As shown above, we investigated whether IgG reactive to each of the 11 EZH2-derived peptides could be detected in the plasma of 10 prostate cancer patients. These patients were not limited to the HLA-A24+ subjects, because peptide-specific IgG was not restricted to MHC class I molecules, as reported previously (22). The mean+2 SD value (OD: 0.04), which was determined as the level of IgG reactive to the HIV peptide in plasma from HIV-negative healthy donors, was used as a cut-off value at a 1:100 diluted plasma in the ELISA. The results are shown in Table 2.

TABLE 2

Humoral response to the EZH2 peptides

| Peptide | Prostate cancer patient | | | | | | | | | | Total |
|---|---|---|---|---|---|---|---|---|---|---|---|
| | #1 | #2 | #3 | #4 | #5 | #6 | #7 | #8 | #9 | #10 | |
| EZH2-291 | 0.040 | 0.041 | 0.074 | — | — | — | — | 0.067 | — | — | 4/10 |
| EZH2-735 | — | 0.050 | — | 0.120 | — | 0.045 | 0.060 | 0.144 | — | — | 5/10 |
| EZH2-657 | — | — | — | 0.106 | — | — | — | 0.076 | — | — | 2/10 |
| EZH2-446 | — | — | — | — | — | — | — | — | — | — | 0/10 |
| EZH2-170 | — | — | — | — | — | — | — | 0.043 | — | — | 1/10 |
| EZH2-90 | — | — | — | — | — | — | — | — | — | — | 0/10 |
| EZH2-660 | — | 0.105 | — | — | — | — | — | — | — | 0.058 | 2/10 |
| EZH2-243 | 0.055 | 0.080 | — | — | — | — | 0.041 | 0.150 | 0.089 | 0.067 | 6/10 |
| EZH2-725 | — | 0.049 | — | — | — | — | — | 0.056 | — | — | 2/10 |
| EZH2-657 | — | — | — | — | — | — | — | — | — | 0.0625 | 1/10 |
| EZH2-119 | — | — | — | — | — | — | — | 0.047 | — | — | 1/10 |

IgG reactive to a corresponding was judged to be positive when a difference of OD at a 1:100-diluted plasma was more than 0.04, which was the mean + 2SD value.

Figure 1A:
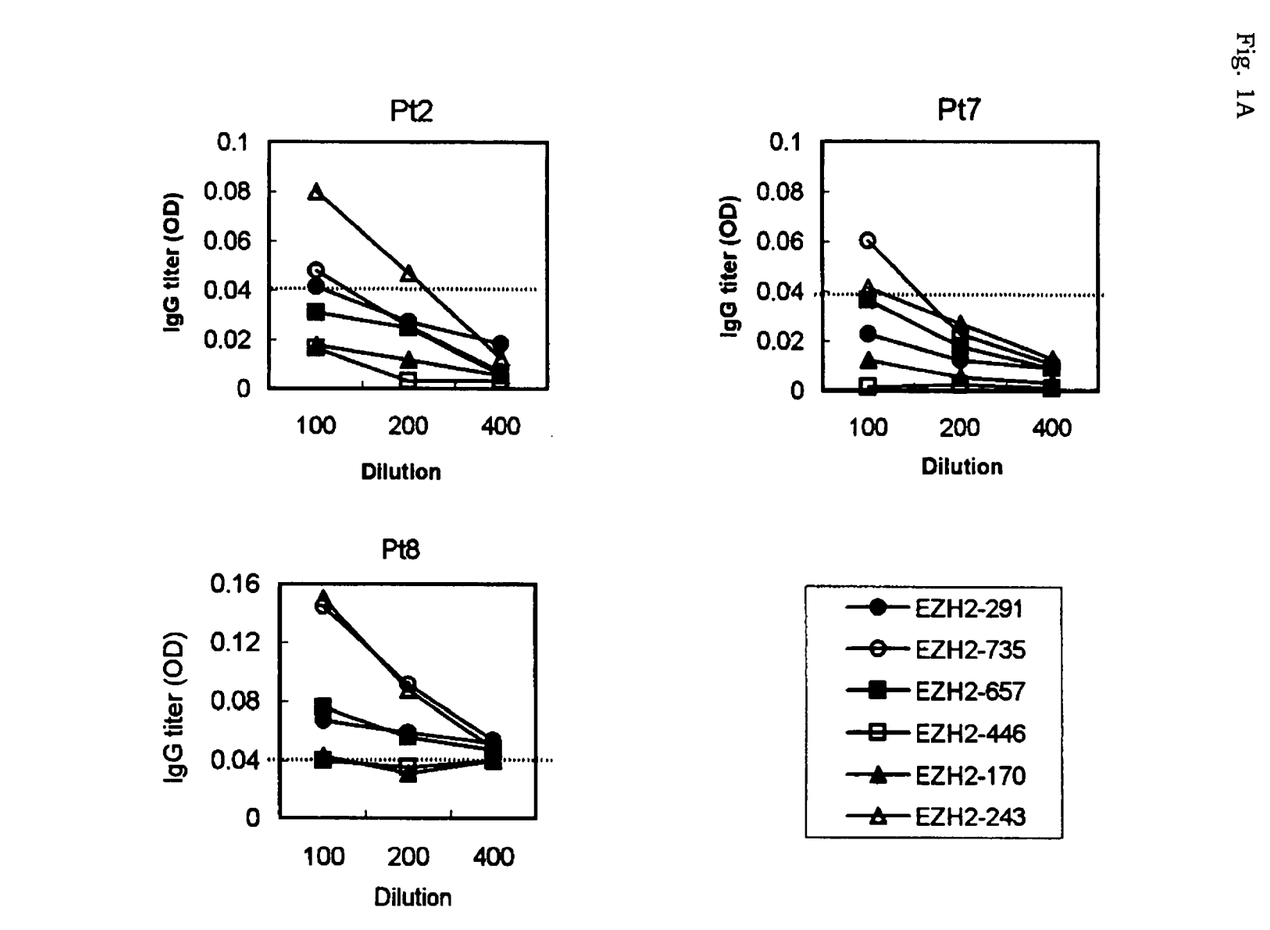
FIG. 1A is a graph showing the levels of IgG reactive to EZH2 peptides in the plasma from patients 2, 7, and 8 as examined by ELISA. The values represent OD. The cut-off level (OD: 0.04) was determined based on the levels of anti-HIV peptide IgG in HIV-negative healthy donors.
Figure 1B:
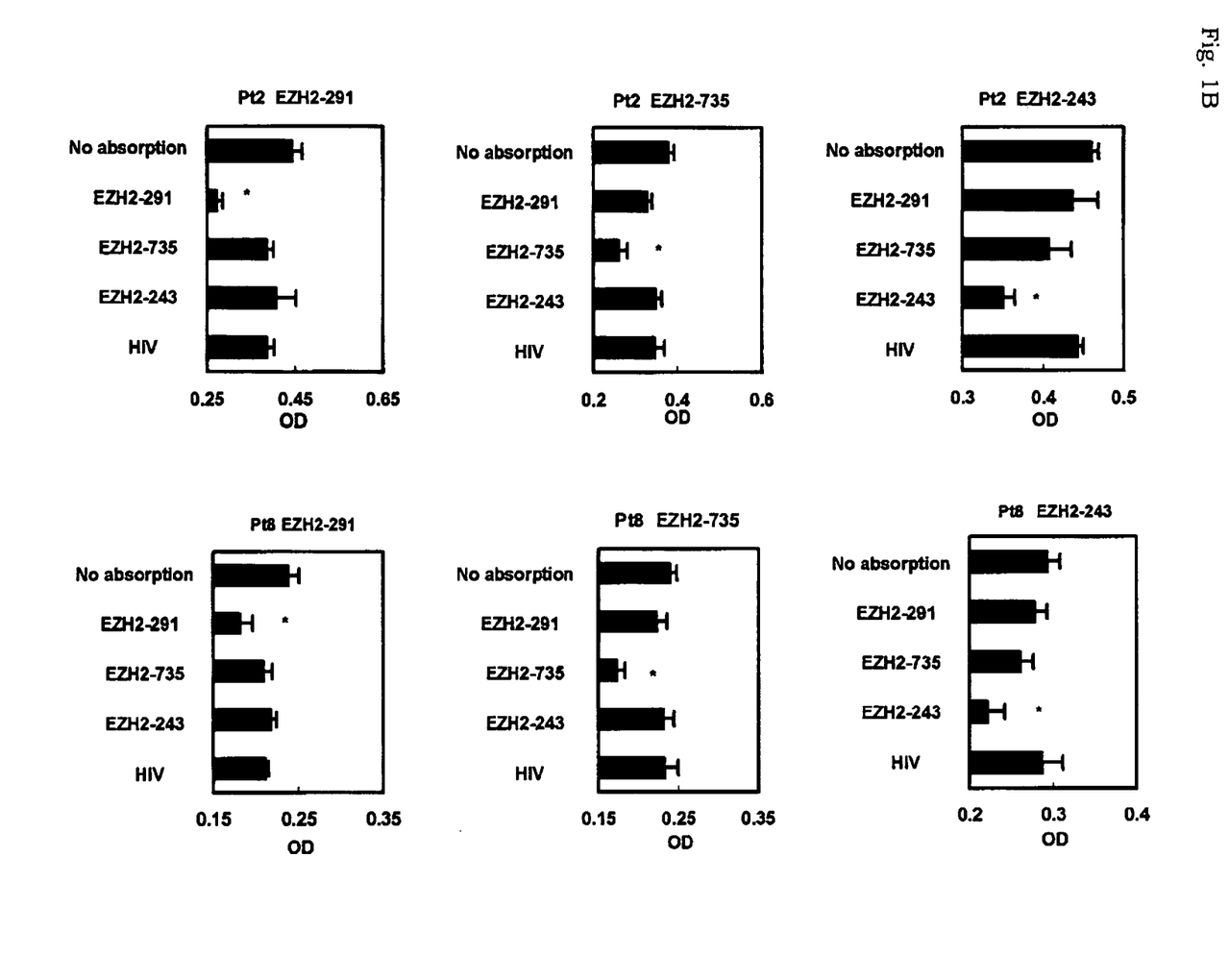
FIG. 1B is a graph showing that the level of IgG reactive to each of these EZH2 peptides was decreased by culturing in corresponding peptide-coated plates.

As a result, IgGs reactive to the EZH2-291, EZH2-735, and EZH2-243 peptides were detected in the plasma of 4, 5, and 6 of 10 patients, respectively. These 3 EZH2 peptides were recognized by IgG more efficiently than the other 8 EZH2 peptides. Eight patients other than patients 4 and 6 were diagnosed to suffer from bone metastases (data not shown). The representative results of patients 2, 7, and 8 are shown in FIG. 1A. Then, the plasma samples from patients 2 and 8 were cultured in plates that were pre-coated with the indicated peptides, and the levels of IgG reactive to the indicated EZH2 peptide in the resultant supernatants were determined by ELISA. The level of IgG reactive to each of these EZH2 peptides was decreased by culturing in corresponding peptide-coated plates, but not in irrelevant peptide-coated plates (FIG. 1B).

These results indicate that the ELISA system detected peptide-specific IgG in an antigen-specific manner. Taken together, these results indicated that these 3 EZH2 peptides (EZH2-291, EZH2-735, and EZH2-243) can be efficiently recognized by IgG in the plasma of prostate cancer patients.

Example 2

Assay for EZH2 Peptide-Specific CTLs in PBMCs from Cancer Patients

We next determined whether these 3 EZH2 peptides had the potential to generate peptide-specific CTLs from the PBMCs of HLA-A24+ cancer patients.

The assay for the detection of peptide-specific CTLs in PBMCs was performed according to a previously reported method (21). In brief, PBMCs ($1 \times 10^5$ cells/well) were incubated with 10 μg/ml of each peptide in a U-bottom-type 96-well microculture plate (Nunc, Roskilde, Denmark) at a volume of 200 μl of culture medium. The culture medium consisted of 45% RPMI-1640, 45% AIM-V medium (Gibco BRL, Grand Island, N.Y.), 10% FCS, 100 U/ml of interleukin (IL)-2, and 0.1 mM MEM nonessential amino acid solution (Gibco BRL, Grand Island, N.Y.). Half of the culture medium was removed and replaced with new medium containing a corresponding peptide (20 μg/ml) every 3 days. On the $15^{th}$ day of culture, the cultured cells were separated into 4 wells, and two of which were used for EZH2 peptide-pulsed C1R-A24 cells, and the other two of which were used for the HIV peptide-pulsed C1R-A24 cells. C1R-A24 is an HLA-A*2402-expressing subline of C1R lymphoma (Oiso M, Eura M, Katsura F, Takiguchi M, Sobao Y, Masuyama K, Nakashima M, Itoh K, Ishikawa T. A newly identified MAGE-3-derived epitope recognized by HLA-A24-restricted cytotoxic T lymphocytes. Int. J. Cancer 81: 387–394, 1999, this reference is incorporated herein by reference). After an 18-hr incubation period, the supernatants were collected and the level of IFN-γ was determined by ELISA. The EZH2-170 peptide was included in this experiment as an EZH2 peptide that was less frequently recognized by the humoral immune system.

The results are shown in Table 3. The values that showed more than 100 pg/ml IFN-γ production and P<0.05 are underlined in this table.

TABLE 3

Reactivity of EZH2 peptide-stimulated PBMCs from HLA A24⁺ prostate cancer patients

| | Peptides | | | | | |
|---|---|---|---|---|---|---|
| Patient | EZH2-291 | EZH2-735 | EZH2-243 | EZH2-170 | Flu | EBV |
| | IFN-γ production (pg/ml) | | | | | |
| #11 | <u>111</u> | <u>239</u> | <u>124</u> | 10 | <u>1638</u> | <u>597</u> |
| #12 | 67 | 54 | 25 | 15 | <u>186</u> | 36 |
| #13 | <u>1597</u> | <u>236</u> | 0 | <u>181</u> | 75 | 42 |
| #14 | <u>276</u> | 26 | 13 | 35 | 58 | <u>971</u> |
| #15 | <u>319</u> | <u>168</u> | 27 | 10 | 25 | <u>197</u> |
| #16 | <u>463</u> | <u>460</u> | 27 | 30 | <u>441</u> | <u>263</u> |
| #17 | 85 | 22 | 44 | 87 | 35 | <u>111</u> |
| #18 | <u>132</u> | 0 | 13 | 0 | 30 | 25 |
| #19 | 0 | 10 | 71 | 16 | 24 | 14 |
| #20 | 12 | N.D. | <u>171</u> | 82 | 26 | 10 |
| Total | 6/10 | 4/9 | 2/10 | 1/10 | 3/10 | 5/10 |

The PBMCs of HLA-A24⁺ prostate cancer patients were stimulated in vitro with the indicated EZH2 peptide.
On day 15, the cultured PBMCs were tested for their reactivity to C1R-A24 cells, which were pre-pulsed with a corresponding peptide or the HIV peptide.
The values represent the mean of 2 wells, and the background IFN-γ production in response to the HIV peptide was subtracted.
Significant values (p < 0.05 by two-tailed Student's t-test and >100 pg/ml of IFN-γ production) are underlined.
N.D., not done.

The result was that the EZH2-291 and EZH2-735 peptides induced peptide-specific CTLs in 6 of 10 and 4 of 9 cancer patients, respectively. The EZH2-243 peptide induced peptide-specific CTLs in 2 of 10 cancer patients, and the EZH2-170 peptide induced peptide-specific CTLs in 1 of 10 cancer patients. Patients 11, 14, and 20 were diagnosed to suffer from bone metastases (data not shown). These results indicate that both the EZH2-291 and EZH2-735 peptides have the potential to efficiently induce peptide-specific CTLs from HLA-A24⁺ prostate cancer patients, even with bone metastases.

Example 3

Induction of Prostate Cancer-reactive CTLs from HLA-A24⁺ Cancer Patients 3.1 Detection for the Expression of EZH2 Gene in Cancer Cell Lines We further determined whether these EZH2 peptide-stimulated PBMCs showed any cytotoxicity against EZH2-expressing cancer cells. Before assay of cytotoxicity, the expression of EZH2 gene in cancer cell lines, the LNCaP cells and PC93 cells, and PBMCs (negative control) was examined using the RT-PCR method. The LNCaP is an HLA-A24-negative prostate cancer cell line (ATCC number CRL-1740), and the PC93 is another prostate cancer cell line (23). The RT-PCR method was carried out as follows. Total RNA was isolated from the cells using RNAzol™ B (Tel-Test Inc., Friendswood, Tex.). The cDNA was prepared using the SuperScript™ Preaamplification System for First Strand cDNA Synthesis (Invitrogen), and it was amplified using the primers: 5'-AATGTGGAATGGAGTGGTGC-3' (sense) [SEQ ID NO: 15] and 5'-ACGAACTGTCACAAG-GCTGC-3'(anti-sense) for EZH2 [SEQ ID NO: 16], and 5'-ACAACAGCCTCAAGATCATCAG-3'(sense) [SEQ ID NO: 17] 5'-GGTCCACCACTGACACGTTG-3'(anti-sense) [SEQ ID NO: 18] for glyceraldehydes 3-phosphate dehydrogenase (GAPDH). PCR was performed using Taq DNA polymerase in a DNA thermal cycler (iCycler, Bio-Rad Laboratories, Hercules, Calif.) for 28 cycles of 94° C. for 1 min, 60° C. for 1 min, and 72° C. for 1 min.

Figure 2:
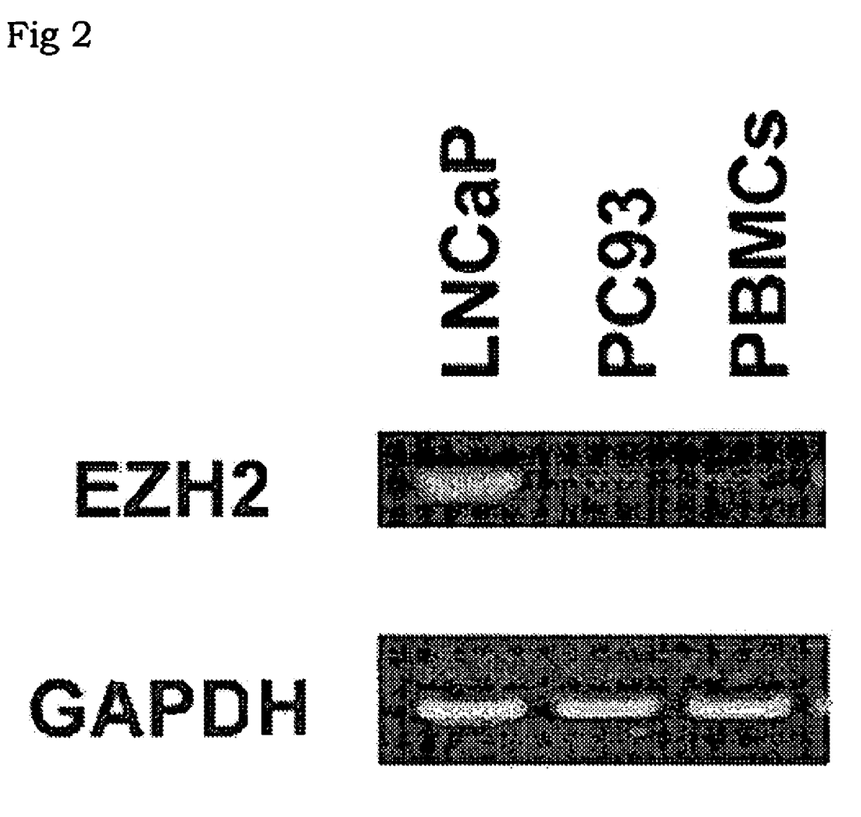
FIG. 2 is a photograph showing the mRNA expression of EZH2 in the LNCaP cells, PC93 cells, and PBMCs as examined by the RT-PCR method.

The result is shown in FIG. 2. As shown in FIG. 2, the LNCaP cells were clearly positive for the EZH2 mRNA expression. However, expression of EZH2 mRNA in PC-93 cells was very faint, and was almost the same as that in normal PBMCs included as a negative control.

3.2 Cytotoxicity of Peptide-stimulated PBMCs Against Three Targets

To investigate HLA-A24-restricted cytotoxicity, the level of cytotoxicity against the LNCaP was compared with the level of cytotoxicity against its transfectant, LNCaP-A24, which is a subline that transfected with the HLA-A*2402 gene and express the gene stably (Yao A, Harada M, Matsueda S, Ishihara Y, Shomura H, Noguchi M, Matsuoka K, Hara I, Kamidono S, Itoh K, Identification of parathyroid hormone-related protein-derived peptides immunogenic in human histocompatibility leukocyte antigen-A24⁺ prostate cancer patients, British Journal of Cancer, 91:287–296, 2004, this reference is incorporated herein by reference). All cell lines were maintained in RPMI-1640 medium (Gibco BRL, Grand Island, N.Y.) supplemented with 10% FCS.

Figure 3:
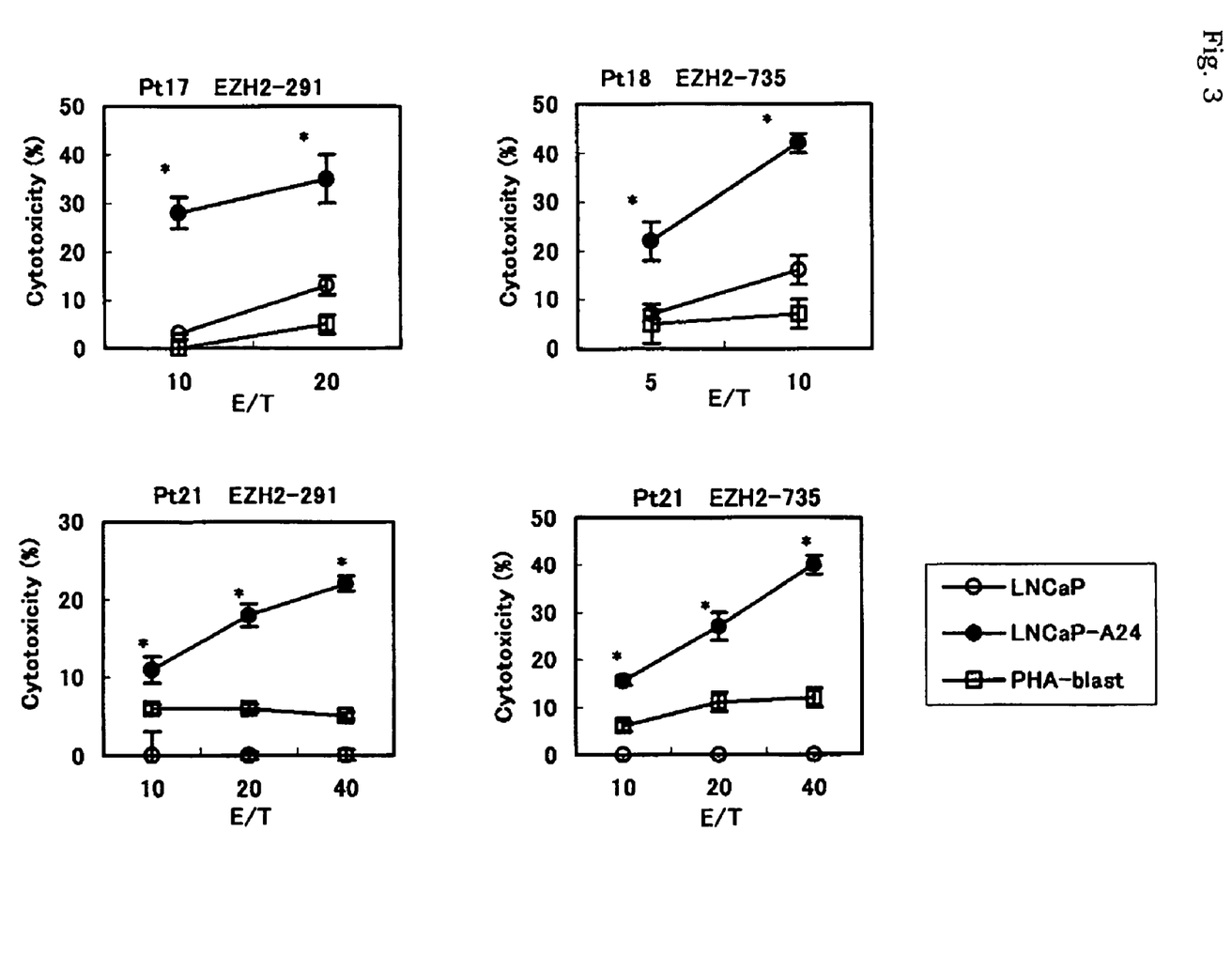
FIG. 3 is a graph showing the cytotoxicity of EZH2 peptide-stimulated PBMCs from 3 HLA-A24+ prostate cancer patients toward 3 different targets, LNCaP cells (HLA- A24⁻), LNCaP-A24 cells (HLA-A24⁺), and PHA-blastoid T cells (HLA-A24⁺), in a 6-hr $^{51}$Cr-release assay. *P<0.05 was considered statistically significant.

The PBMCs from 3 HLA-A24⁺ prostate cancer patients were then stimulated in vitro with the indicated EZH2 peptide, and examined for their cytotoxicity against HLA-A24⁻ LNCaP cells, HLA-A24⁺ LNCaP-A24, and HLA-A24⁺ PHA-stimulated T cell blasts. Specifically, after in vitro stimulation with the EZH2 peptides, the peptide-stimulated PBMCs were additionally cultured with 100 U/ml IL-2 for approximately 10 days in 96 round-well plates in order to obtain a sufficient number of cells to carry out a cytotoxicity assay. Then, these cells were tested for cytotoxicity against LNCaP, LNCaP-A24, and PHA-stimulated T cell blasts by a 6-hr $^{51}$Cr-release assay. Two thousand $^{51}$Cr-labeled cells per well were cultured with effector cells in 96 round-well plates at the indicated effector/target ratios. The results are shown in FIG. 3. The EZH2 peptide-stimulated PBMCs exhibited higher levels of cytotoxicity against the HLA-A24⁺ LNCaP-A24 cells than against the HLA-A24− LNCaP cells and HLA-A24⁺ PHA-stimulated T cell blasts.

These results indicated that the EZH2-291 and EZH2-735 peptides have the potential to efficiently induce HLA-A24-restricted and prostate cancer-reactive CTLs from HLA-A24⁺ prostate cancer patients.

Example 4

Figure 4A:
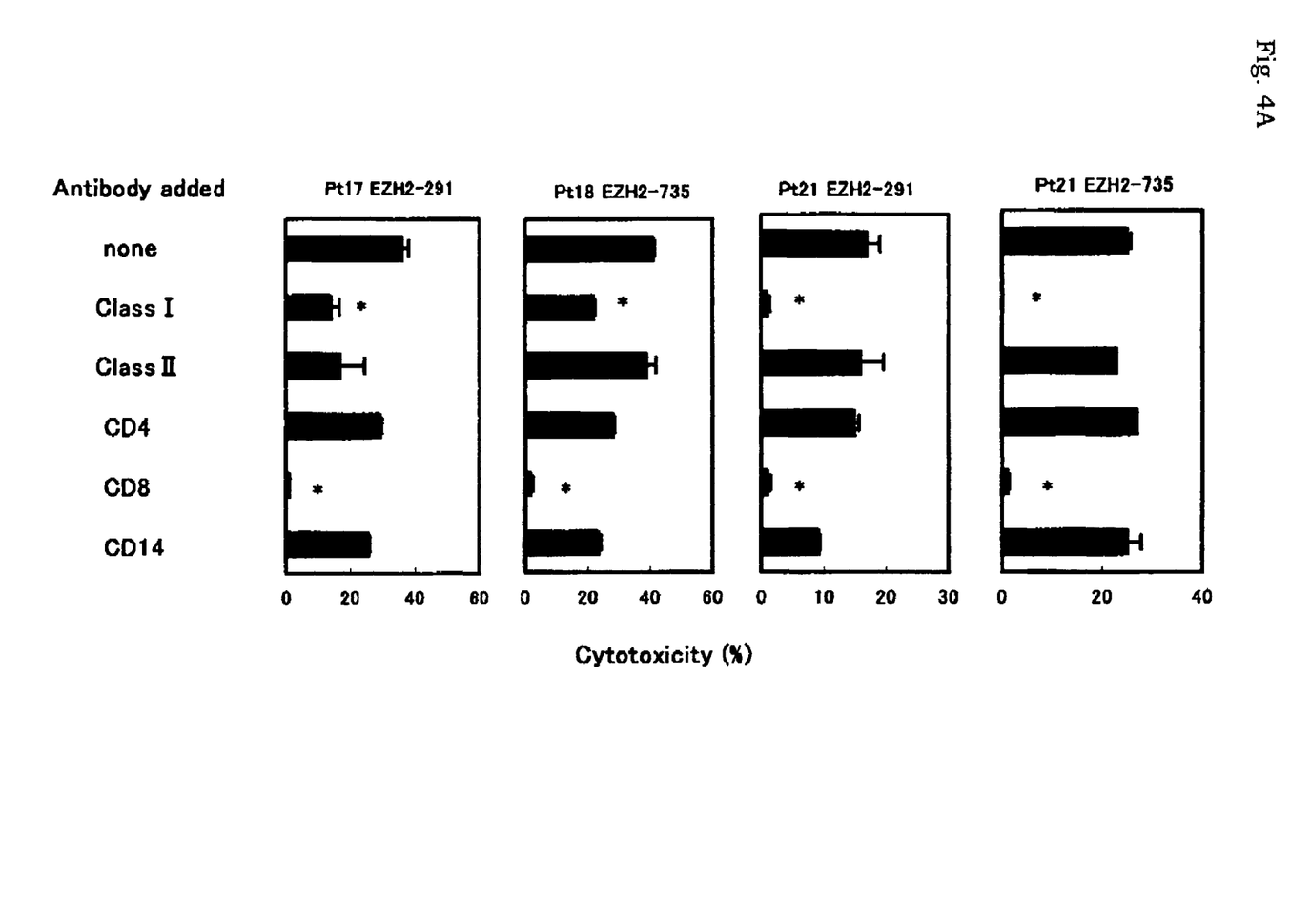
FIG. 4A is a graph showing the inhibition of the cytotoxicity of EZH2 peptide-stimulated PBMCs by various antibodies. The values represent the mean of triplicate assays. *P<0.05 was considered statistically significant.

Peptide-specific and CD8⁺ T Cell-dependent Cytotoxicity of EZH2 Peptide-stimulated PBMCs from Cancer Patients 4.1 Inhibition of the Cytotoxicity of EZH2 Peptide-stimulated PBMCs by Antibodies We further tried to confirm which effector cells were responsible for the cytotoxicity. EZH2 peptide-stimulated PBMCs from patients 17, 18, and 21 were tested for their cytotoxicity against the LNCaP-A24 cells. The 6-hr cytotoxicity assay was performed in the presence of the indicated monoclonal antibody (mAb). The assay was done at an effector/target ratio of 10/1. Either anti-HLA class I (W6/32: mouse IgG2a), anti-HLA-DR (L243: mouse IgG2a), anti-CD4 (Nu-Th/i: mouse IgG1), anti-CD8 (Nu-Ts/c: mouse IgG2a), or anti-CD14 (H14: mouse IgG2a) mAb was added to the wells at a dose of 20 µg/ml at the start of the assay. As a result, the cytotoxicity of the PBMCs from 3 prostate cancer patients, which were stimulated in vitro with each of the EZH2–291 and EZH2-735 peptides, against the LNCaP-A24 cells were significantly inhibited by the addition of anti-class I or anti-CD8 mAb, but not by the addition of anti-class II, anti-CD4, or anti-CD 14 mAb (FIG. 4A).

4.2 Confirmation of the Specificity of EZH2 Peptide-stimulated PBMCs by a Cold Inhibition Assay EZH2 peptide-stimulated PBMCs from patients 17, 18, and 21 were tested for their cytotoxicity against the LNCaP-A24 in the presence of unlabeled C1R-A24 cells, which were pre-loaded with either the corresponding EZH2 peptide or the HIV peptide.

Figure 4B:
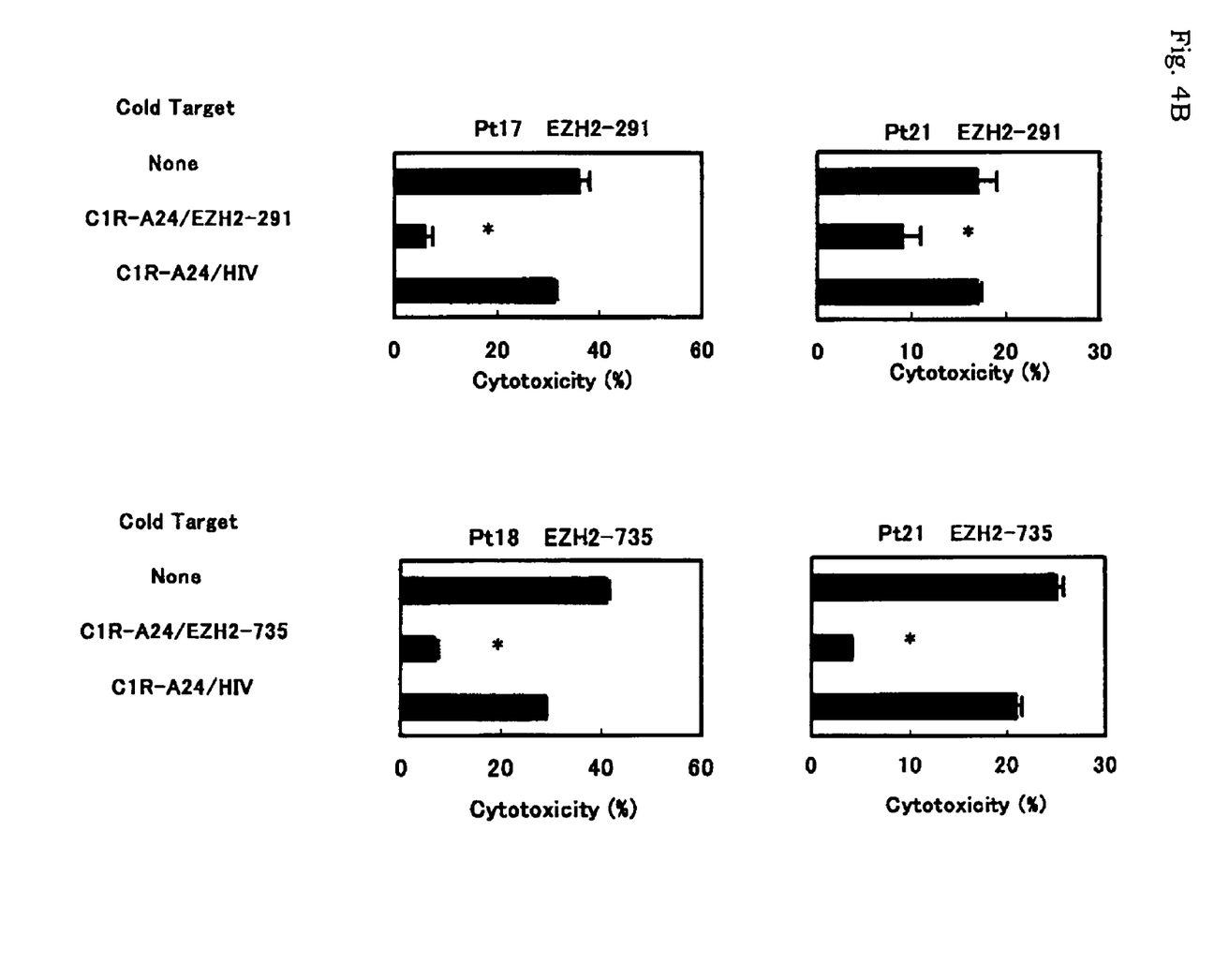
FIG. 4B is a graph showing the inhibition of the cytotoxicity of EZH2 peptide-stimulated PBMCs by cold target cells pre-loaded with the corresponding EZH2 peptide. The values represent the mean of triplicate assays. *P<0.05 was considered statistically significant.

In brief, $^{51}$Cr-labbeled target cells (2×10³ cells/well) were cultured with the CTLs (4×10⁴ cells/well) in 96 round-well plates with 2×10⁴ cold target cells. C1R-A24 cells that were pre-pulsed with either the HIV peptide or a corresponding EZH2 peptide were used as cold targets. The assay was done at an effector/target ratio of 10/1. The cytotoxicity of these EZH2 peptide-stimulated PBMCs against the LNCaP-A24 cells was significantly suppressed by the addition of the relevant peptide-pulsed unlabeled C1R-A24 cells, but not by the addition of the HIV peptide-pulsed unlabeled C1R-A24 cells (FIG. 4B).

Collectively, these results indicate that cytotoxicity of the EZH2 peptide-stimulated PBMCs was mainly ascribed to peptide-specific and CD8⁺ T cells.

REFERENCES

The contents of the references cited in the specification and below are herein incorporated by reference.

1. Greenlee R T, Murray T, Bolden S, Wingo P A. Cancer statistics 2000. CA Cancer J Clin 2000; 50:7–33.
2. Harada M, Noguchi M, Itoh K. Target molecules in specific immunotherapy against prostate cancer. Int J Clin Oncl 2003; 8: 193–199.
3. Gulley J, Chen A P, Dahut W, Arlen P M, Bastian A, Steinberg S M, Tsang K, Panicali D, Poole D, Schlom J, Hamilton M J. Phase I study of a vaccine using recombinant vaccinia virus expressing PSA (rV-PSA) in patients with metastatic androgen-independent prostate cancer. Prostate 2002; 53:109–117.
4. Murphy G., Tjoa B, Ragde H, Kenny G., Boynton A. Phase I clinical trial: T-cell therapy for prostate cancer using autologous dendritic cells pulsed with HLA-A0201-specific peptides from prostate-specific membrane antigen. Prostate 1996; 29:371–380.
5. Tjoa B A, Simmons S J, Bowes V A, Ragde H, Rogers M, Elgamal A, Kenny G M, Cobb O E, Ireton R C, Troychak M J, Salgaller M L, Boynton A L, Murphy G P. Evaluation of phase I/II clinical trials in prostate cancer with dendritic cells and PSMA peptides. Prostate 1998; 36:39–44.
6. Murphy G. P, Tjoa B A, Simmons S J, Jarisch J, Bowes V A, Rogers M, Elgamal A, Kenny G M, Cobb O E, Ireton R C, Troychak M J, Salgaller M L, Boynton A L. Infusion of dendritic cells pulsed with HLA-A2-specific prostate-specific membrane antigen peptides: a phase II prostate cancer vaccine trial involving patients with hormone-refractory metastatic disease. Prostate 1999; 38:73–78.
7. Small E J, Fratesi P, Reese D M, Strang G., Laus R, Peshwa M V, Valon F H. Immunotherapy of hormone-refractory prostate cancer with antigen-loaded dendritic cells. J Clin Oncol 2000; 18:3894–3903.
8. Laible G., Wolf A, Dorn R, Reuter G, Nislow C, Lebersorger A, Popkin D, Pillus L, Jenuwein T. Mammalian homologue of the Polycomb-group gene Enhancer of zeste mediate gene silencing in Drosophila heterochromatin and at S. cerevisiae telomeres. EMBO J 1997; 16:3219–3232.
9. Kleer C G, Cao Q, Varambally S, Shen R, Ota I, Tomlins S A, Ghosh D, Sewalt R G A B, Otte A P, Hayes D F, Sabel M S, Livant D, Weiss S J, Rubin M A, Chinnaiyan A M. EZH2 is a marker of aggressive breast cancer and promotes neoplastic transformation of breast epithelial cells. Proc. Natl Acad Sci USA 2003; 100: 11606–11611.
10. Jacobs J J, Kieboom K, Mario S, DePinho R A, van Lohuizen M. The oncogene and Polycomb-group gene bmi-1 regulates cell proliferation and senescence through the ink4a locus. Nature 1999; 397: 164–8.
11. Jacob J J, Scheijen B, Voncken J W, Kieboom K, Berns A, van Lohuizen M. Bmi-1 collaborates with c-Myc in tumorigenesis by inhibiting c-Myc-induced apoptosis via INK4a/ARF. Genes Dev 1999; 13: 2678–90.
12. Varambally S, Dhanasekaran S M, Zhou M, Barrette T B, Kumar-Sinha C, Sanda M G, Ghosh D, Pienta K J, Sewalt R G A B, Oyye A P, Rubin M A, Chinnaiyan A M. The polycomb group protein EZH2 is involved in progression of prostate cancer. Nature 2002; 419: 624–629.
13. Noguchi M, Mine T, Suetsugu N, Tomiyasu K, Suekane S, Yamada A, Itoh K, Noda S. Induction of cellular and humoral immune responses to tumor cells and peptides in HLA-A24 positive hormone-refractory prostate cancer patients by peptide vaccination. Prostate 2003; 57: 80–92.
14. Tanaka S, Harada M, Mine T, Noguchi M, Gohara R, Azuma K, Tamura M, Yamada A, Morinaga A, Nishikori M, Katagiri K, Itoh K, Yamana H, Hashimoto T. Peptide vaccination for patients with melanoma and other types of cancer based on pre-existing peptide-specific cytotoxic T lymphocyte precursors in the periphery. J Immunother 2003; 26: 357–366.
15. Mine T, Gouhara R, Hida N, Imai N, Azuma K, Rikimaru T, Katagiri K, Nishikori M, Sukehiro A, Nakagawa M, Yamada A, Aizawa H, Shirouzu K, Itoh K, Yamana H. Immunological evaluation of CTL precursor-oriented vaccines for advanced lung cancer patients. Cancer Science 2003; 94: 548–556.

16. Sato Y, Shomura H, Maeda Y, Mine T, Ueno Y, Akasaka Y, Kondo M, Takahashi S, Shinohara T, Katagiri K, Sato M, Okada S, Matsui K, Yamada A, Yamana H, Itoh K, Todo S. Immunogical evaluation of peptide vaccination for patients with gasctirc cancer based on pre-existing cellular response to peptide. Cancer Science 2003; 94: 802–808.
17. Tsuda N, Mochizuki K, Harada M, Sukehiro A, Kawano K, Yamada A, Ushijima K, Sugiyama T, Nishida T, Yamana H, Itoh K, Kamura T. Vaccination with pre-designated or evidence-based peptides for patients with recurrent gynecologic cancers. J. Immuther 2004, 27: 60–72.
18. Nakatsura T, Senju S, Ito M, Nishimura, Y, Itoh K. Cellular and humoral immune responses to a human pancreatic cancer antigen, coactosin-like protein, originally defined by the SEREX method. Eur J Immunol 2002; 32: 826–836.
19. Parker K C, Bednarek M A, Coligan J E. Scheme for ranking potential HLA-A2 binding peptides based on independent binding of individual peptide side-chains. J Immunol 1994; 152: 163–175.
20. Ohkouchi S, Yamada A, Imai N, Mine T, Harada K, Shichijo S, Maeda Y. Saijyo Y, Nukiwa T, Itoh K. Non-mutated tumor rejection antigen peptides elicit type-I allergy in the majority of healthy individuals. Tissue Antigens 2002; 59: 259–272.
21. Hida N, Maeda Y, Katagiri K, Takasu H, Harada M, Itoh K. A new culture protocol to detect peptide-specific cytotixic T lymphocyte precursors in the circulation. Cancer Immunol Immunother 2002; 51: 219–228.
22. Kawamoto N, Yamada A, Ohkouchi S, Maeda T, Tanaka S, Hashimoto T, Saijo Y, Saijo S, Nukiwa T, Shichijo S, Aizawa H. Itoh K. IgG reactive to CTL-directed epitopes of self-antigens is either lacking or unbalanced in atopic dermatitis patients. Tissue Antigens 2003; 61: 352–361.
23. Harada M, Kobayashi K, Matsueda S, Nakagawa M, Noguchi M, Itoh K. Prostate-specific antigen-derived epitopes capable of inducing cellular and humoral responses in HLA-A24$^+$ prostate cancer patients. Prostate 2003; 57: 152–159.
24. Kobayashi K, Noguchi M, Itoh K, Harada M. Identification of a prostate-specific membrane antigen-derived peptide capable of eliciting both cellular and humoral immune responses in HLA-A24$^+$ prostate cancer patients. Cancer Science 2003; 94: 622–627.
25. Matsueda S, Kobayashi K, Nonaka Y, Noguchi M, Itoh K, Harada M. Identification of new prostate stem cell antigen-derived peptides immunogenic in HLA-A2+patients with hormone-refractory prostate cancer. Cancer Immunol Immunother 2004; 53: 479–489.
26. Inoue Y, Takaue Y, Takei M, Kato K, Kanai S, Harada Y, Tobisu K, Noguchi M, Kakizoe T, Itoh K, Wakasugi H. Induction of tumor specific cytotoxic T lymphocytes in prostate cancer using prostatic acid phosphatase derived HLA-A2402 binding peptide. J Urol 2001; 166:1508–1513.
27. Imanishi T, Akazawa T, Kimura A. Allele and haplotype frequencies for HLA and complement loci in various ethnic groups. In: Tsuji K, Aizawa M, Sasazuki T, editors. HLA 1991. Vol. 1 Oxford: Oxford Scientific Publications; 1992. pp 1065–1220.

What is claimed is:

1. A peptide consisting of the amino acid sequence shown in SEQ ID NO:2.

* * * * *

```
                              SEQUENCE LISTING

<160> NUMBER OF SEQ ID NOS: 18

<210> SEQ ID NO 1
<211> LENGTH: 9
<212> TYPE: PRT
<213> ORGANISM: Artificial
<220> FEATURE:
<223> OTHER INFORMATION: EZH2 291-299

<400> SEQUENCE: 1

Lys Tyr Asp Cys Phe Leu His Pro Phe
1               5

<210> SEQ ID NO 2
<211> LENGTH: 9
<212> TYPE: PRT
<213> ORGANISM: Artificial
<220> FEATURE:
<223> OTHER INFORMATION: EZH2 735-743

<400> SEQUENCE: 2

Lys Tyr Val Gly Ile Glu Arg Glu Met
1               5

<210> SEQ ID NO 3
<211> LENGTH: 9
<212> TYPE: PRT
<213> ORGANISM: Artificial
<220> FEATURE:
<223> OTHER INFORMATION: EZH2 657-665

<400> SEQUENCE: 3
```

Val Tyr Asp Lys Tyr Met Cys Ser Phe
1               5

<210> SEQ ID NO 4
<211> LENGTH: 9
<212> TYPE: PRT
<213> ORGANISM: Artificial
<220> FEATURE:
<223> OTHER INFORMATION: EZH2 446-454

<400> SEQUENCE: 4

Thr Tyr Tyr Asp Asn Phe Cys Ala Ile
1               5

<210> SEQ ID NO 5
<211> LENGTH: 9
<212> TYPE: PRT
<213> ORGANISM: Artificial
<220> FEATURE:
<223> OTHER INFORMATION: EZH2 170-178

<400> SEQUENCE: 5

Ile Phe Val Glu Leu Val Asn Ala Leu
1               5

<210> SEQ ID NO 6
<211> LENGTH: 9
<212> TYPE: PRT
<213> ORGANISM: Artificial
<220> FEATURE:
<223> OTHER INFORMATION: EZH2 90-98

<400> SEQUENCE: 6

Asp Phe Pro Thr Gln Val Ile Pro Leu
1               5

<210> SEQ ID NO 7
<211> LENGTH: 10
<212> TYPE: PRT
<213> ORGANISM: Artificial
<220> FEATURE:
<223> OTHER INFORMATION: EZH2 660-669

<400> SEQUENCE: 7

Lys Tyr Met Cys Ser Phe Leu Phe Asn Leu
1               5                   10

<210> SEQ ID NO 8
<211> LENGTH: 10
<212> TYPE: PRT
<213> ORGANISM: Artificial
<220> FEATURE:
<223> OTHER INFORMATION: EZH2 243-252

<400> SEQUENCE: 8

Lys Tyr Lys Glu Leu Thr Glu Gln Gln Leu
1               5                   10

<210> SEQ ID NO 9
<211> LENGTH: 10
<212> TYPE: PRT
<213> ORGANISM: Artificial
<220> FEATURE:
<223> OTHER INFORMATION: EZH2 725-734

<400> SEQUENCE: 9

```
Asp Tyr Arg Tyr Ser Gln Ala Asp Ala Leu
1               5                   10

<210> SEQ ID NO 10
<211> LENGTH: 10
<212> TYPE: PRT
<213> ORGANISM: Artificial
<220> FEATURE:
<223> OTHER INFORMATION: EZH2 657-666

<400> SEQUENCE: 10

Val Tyr Asp Lys Tyr Met Cys Ser Phe Leu
1               5                   10

<210> SEQ ID NO 11
<211> LENGTH: 10
<212> TYPE: PRT
<213> ORGANISM: Artificial
<220> FEATURE:
<223> OTHER INFORMATION: EZH2 119-128

<400> SEQUENCE: 11

Asn Phe Met Val Glu Asp Glu Thr Val Leu
1               5                   10

<210> SEQ ID NO 12
<211> LENGTH: 10
<212> TYPE: PRT
<213> ORGANISM: Artificial
<220> FEATURE:
<223> OTHER INFORMATION: Flu virus-derived peptide

<400> SEQUENCE: 12

Arg Phe Tyr Ile Gln Met Cys Tyr Glu Leu
1               5                   10

<210> SEQ ID NO 13
<211> LENGTH: 9
<212> TYPE: PRT
<213> ORGANISM: Artificial
<220> FEATURE:
<223> OTHER INFORMATION: EBV-derived peptide

<400> SEQUENCE: 13

Thr Tyr Gly Pro Val Phe Met Cys Leu
1               5

<210> SEQ ID NO 14
<211> LENGTH: 11
<212> TYPE: PRT
<213> ORGANISM: Artificial
<220> FEATURE:
<223> OTHER INFORMATION: HIV-derived peptide

<400> SEQUENCE: 14

Arg Tyr Leu Arg Asp Gln Gln Leu Leu Gly Ile
1               5                   10

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
aatgtggaat ggagtggtgc                                           20
```

```
<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
acgaactgtc acaaggctgc                                                   20

<210> SEQ ID NO 17
<211> LENGTH: 22
<212> TYPE: DNA
<213> ORGANISM: Artificial
<220> FEATURE:
<223> OTHER INFORMATION: Primer

<400> SEQUENCE: 17
acaacagcct caagatcatc ag                                                22

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
ggtccaccac tgacacgttg                                                   20
```